(12) United States Patent
Pruckner et al.

(10) Patent No.: US 10,932,883 B2
(45) Date of Patent: Mar. 2, 2021

(54) COUPLING ELEMENT FOR ATTACHING A MEDICAL OR DENTAL INSTRUMENT TO A CONTROL OR SUPPLY UNIT

(71) Applicant: W&H Dentalwerk Bürmoos GmbH, Bürmoos (AT)

(72) Inventors: Christian Pruckner, Vienna (AT); Bernhard Silberer, Michaelbeuern (AT); Johann Eibl, Mattighofen (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 355 days.

(21) Appl. No.: 15/712,081

(22) Filed: Sep. 21, 2017

(65) Prior Publication Data

US 2018/0008372 A1   Jan. 11, 2018

Related U.S. Application Data

(63) Continuation of application No. PCT/EP2016/056301, filed on Mar. 23, 2016.

(30) Foreign Application Priority Data

Mar. 27, 2015  (EP) .................................. 15161217

(51) Int. Cl.
*A61C 1/08* (2006.01)
*A61C 1/00* (2006.01)
(Continued)

(52) U.S. Cl.
CPC ............ *A61B 90/98* (2016.02); *A61C 1/0015* (2013.01); *A61C 1/088* (2013.01); *A61B 2017/00482* (2013.01)

(58) Field of Classification Search
CPC ................................ A61B 90/30; A61C 1/088
See application file for complete search history.

(56) References Cited

U.S. PATENT DOCUMENTS 5,074,785 A * 12/1991 Malata, Jr. ............. A61C 1/088
                                                    433/29
2003/0165794 A1* 9/2003 Matoba .................. A61B 90/90
                                                   433/114
(Continued)

FOREIGN PATENT DOCUMENTS

EP        2184028        5/2010
EP        2514386        10/2012
(Continued)

OTHER PUBLICATIONS

International Search Report for PCT-EP2016-056301, dated Jun. 2, 2016.

*Primary Examiner* — Gary Jackson
*Assistant Examiner* — Zahed Kabir
(74) *Attorney, Agent, or Firm* — Klarquist Sparkman, LLP

(57) ABSTRACT

A medical or dental instrument part having a coupling device for connecting the instrument part to a control, regulating or supply unit, a memory device that can be operated with electrical power for storing identification data and/or operating and/or care data of the instrument part and at least one electrical line, which is provided for supplying electrical power to a lighting device that is provided on the instrument part or can be connected to the instrument part for operating the lighting device and for supplying electrical power to the memory device for operating the memory device. In addition, a medical or dental treatment device having such a medical or dental instrument part and a corresponding method for supplying electrical power to a lighting device and to a memory device by at least one electrical line are provided.

18 Claims, 2 Drawing Sheets

(51) Int. Cl.
*A61B 17/00* (2006.01)
*A61B 90/98* (2016.01)

(56) References Cited

U.S. PATENT DOCUMENTS

| | | | | |
|---|---|---|---|---|
| 2004/0209223 | A1* | 10/2004 | Beier | A61B 17/1626 433/99 |
| 2008/0176181 | A1* | 7/2008 | Putz | A61C 1/00 433/29 |
| 2010/0248177 | A1* | 9/2010 | Mangelberger | A61C 1/12 433/25 |
| 2015/0037751 | A1* | 2/2015 | Motoyama | A61C 1/088 433/29 |
| 2016/0058525 | A1* | 3/2016 | Nichols | A61C 1/088 433/27 |

FOREIGN PATENT DOCUMENTS

| | | | | |
|---|---|---|---|---|
| EP | 2727552 A1 | * | 5/2014 | |
| EP | 2774572 A1 | * | 9/2014 | A61C 1/088 |
| EP | 2727552 | | 5/2017 | |
| JP | 2002035009 | | 2/2002 | |
| JP | 2002336281 | | 11/2002 | |

\* cited by examiner

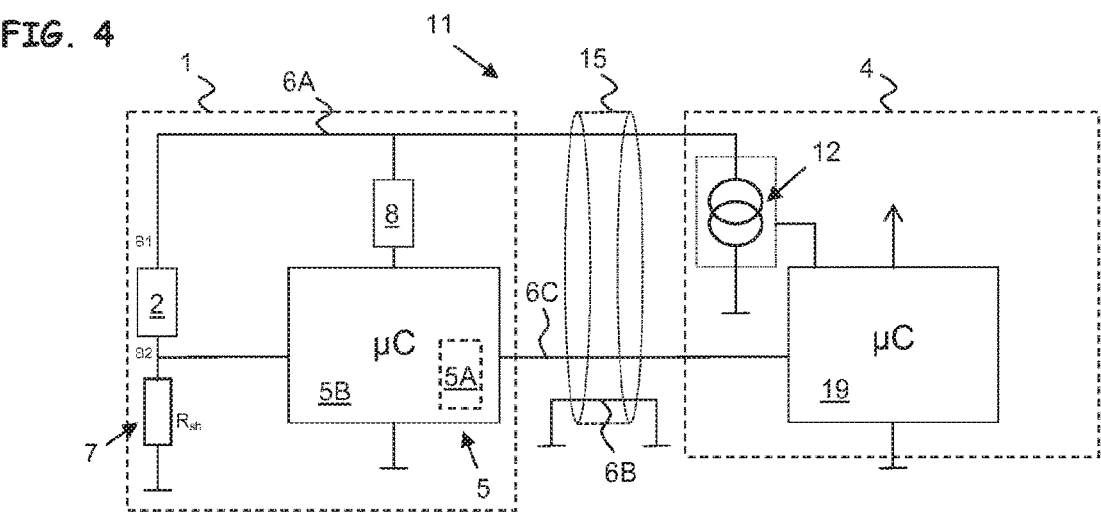

COUPLING ELEMENT FOR ATTACHING A MEDICAL OR DENTAL INSTRUMENT TO A CONTROL OR SUPPLY UNIT

CROSS REFERENCE TO RELATED APPLICATION

This application is a U.S. bypass continuation of International Application No. PCT/EP2016/056301, filed Mar. 23, 2016, which in turn claims priority from pending European Patent Application No. 15161217.3, filed Mar. 27, 2015, which are incorporated herein by reference.

BACKGROUND

Field

The present application relates to a medical or dental instrument part with a memory device that can be operated with electrical power for storing identification data and/or operating data and/or care data of or for the instrument part.

Description of Prior Art

A medical or dental instrument part with a memory device that can be operated with electrical power is known from the patent application US 2003/0165794 A1 (also published as U.S. Pat. No. 6,899,538), for example. This memory device is part of an identification signal output device for active output of identification signals to identify the instrument part so that a circuit of a control, regulating or supply unit automatically recognizes the instrument part and supplies it or drives it accordingly. The power supply and communication between the memory device and the drive circuit are hardwired and take place via electrical lines, which electrically connect the memory device and the control, regulating or supply unit.

SUMMARY

An object of the present application is to improve the design of a medical or dental instrument part with regard to the hardwired power supply and communication link/data transmission between the memory device and the control, regulatory or supply unit. In particular, the design of the instrument part should be simple and components forming the power supply and communication link between the memory device and the control, regulating or supply unit should take up little space and ensure a reliable power supply and data transmission.

These objects are achieved by a medical or dental instrument part, by a medical or dental treatment device and by a method for operating a medical or dental instrument part or a medical or dental treatment device having the features described below. The medical or dental instrument part comprises: a coupling device for connection of the instrument part to a control, regulating or supply unit, a memory device that can be operated with electrical power for storing identification data and/or operating data and/or care data of the instrument part and at least one electrical line, which is provided for supplying electrical power to a lighting device that is provided on the instrument part or is or can be connected to the instrument part for operation of the lighting device and for supplying electrical power to the memory device for operation of the memory device.

The design of the instrument part is greatly simplified due to the fact that at least one electrical line is provided for supplying electrical power to the lighting device for operation of the lighting device and for supplying electrical power to the memory device for operating the memory device. Thus, for example, the number of electrical lines in the instrument part is reduced. In particular the design of the coupling device for connecting the instrument part to a control, regulating or supply unit is greatly simplified because the number of electrical contacts on the interface of the coupling device is reduced.

The at least one electrical line which is provided for supplying electrical power to the lighting device that is provided on the instrument part or can be connected to the instrument part for operating the lighting device and for supplying electrical power to the memory device for operating the memory device is preferably designed as a joint or shared electrical line, in particular as a joint electrical line for the lighting device and the memory device. The lighting device and the memory device are thus in particular electrically connected to the (joint) electrical line. A branching point, from which a first electrical branch line extends to the memory device and a second electrical branch line extends to the lighting device, is provided in particular.

The at least one (joint) electrical line is preferably designed as a wire line and/or as an electrical line printed on a circuit board.

The term "medical or dental instrument part" is understood below as follows: a medical or dental element that can be held in a hand, a hand grip element, a straight handpiece, an angled or bent handpiece or a contra-angled handpiece, an adapter, a coupling element, a drive element in particular an air motor or an electric motor or a supply tube or a part of one of the elements listed above.

The instrument part preferably comprises a medical or dental handpiece or at least one part thereof including: a drive element that can be set in rotation for driving a tool that is releasably connectable to the handpiece, a coupling device for connecting the handpiece to a control, regulating or supply unit, a memory device that can be operated with electrical power for storing identification data and/or operating data and/or care data of the handpiece, a lighting device that can be operated with electrical power for emitting radiation to a treatment site, and at least one (joint) electrical line, which is provided for supplying electrical power to the lighting device for operating the lighting device and for supplying electrical power to the memory device for operating the memory device.

The coupling device for connecting the instrument part to a control, regulating or supply unit is in particular designed as a releasable coupling device, so that the instrument part can be separated from the control, regulating or supply unit. The coupling device is designed, for example, as a plug coupling or as a pivoting coupling, so that the instrument part can be rotated in relation to the control, regulating or supply unit, when the instrument part is connected to the control, regulating or supply unit via the coupling device.

The coupling device comprises in particular an end face, on which at least one electrical contact that is connected to the at least one joint electrical line, is provided. When two joint electrical lines are provided, there are preferably two electrical contacts disposed on the end face of the coupling device, wherein one of the two electrical contact is connected to one of the two joint electrical lines, respectively. When at least one separate optical or electrical line is provided for transmitting identification data and/or operating data and/or care data, then an optical or electrical contact that is connected to this at least one electrical line for data transmission is preferably provided accordingly.

The at least one electrical contact or the electrical contacts is/are preferably releasably connected to the control, regulating or supply unit. The at least one electrical contact is, for example, preferably designed as a pin-shaped electrical contact, as a spring contact, as a sliding contact or as a ring-shaped electrical contact surrounding a component of the coupling device.

The memory device comprises either a read-only memory (ROM) or preferably a readable and writable memory. The memory device is designed in particular as a digital memory device for storage and/or readout and/or processing of digital data.

In particular identification data and/or operating data and/or care data assigned to that instrument part in which the memory device is disposed, is/are preferably stored or can be stored in the memory device of the instrument part. Alternatively, it is also conceivable that identification data and/or operating data and/or care data from another instrument part other than the instrument part, in which the memory device is disposed is or can be stored additionally or exclusively in the memory device.

The memory device preferably comprises a memory element and a microcontroller or microcomputer, which is/are optionally designed as one component or as two separate components electrically connected to one another. If the memory element and the microcontroller are embodied separately from one another, then it is possible to position them at different locations in/on the instrument part so that the arrangement of the two components in an instrument part with a small internal volume is facilitated.

The memory device with the microcontroller is preferably designed for active output of a digital signal or digital data. The memory device with the microcontroller also comprises in particular software enabling it to receive, send, process, store data and/or to carry out independent control steps.

The supply of electrical power to the lighting device and the memory device and preferably the (digital) data transmission over the at least one (joint) electrical line is/are implementable, for example, by modulation and/or digital multiplexing and/or by time offset transmission or sending of digital data and/or electrical power, in particular being implementable with the help of the microcontroller of the memory device.

The lighting device that is provided on the instrument part or can be connected to the instrument part preferably comprises one or more light sources, for example, optical semiconductor elements, in particular light-emitting diodes (LEDs). The lighting device preferably comprises a plurality of light sources, wherein at least one first light source (LED) emits a first wavelength or a first wavelength range, and at least one second light source (LED) emits a second wavelength or a second wavelength range, which differs from the first wavelength or the first wavelength range. The first light source and the second light source are preferably disposed in different electrical current directions. A switching device for optional operation of the first light source or the second light source and/or for optional emission of electromagnetic radiation by the first light source or by the second light source is especially preferably provided on the instrument part. In particular the switching device is connected to the microcontroller or designed as part of the microcontroller or is provided on an element that is or can be connected to the instrument part, for example, the control, regulating or supply unit. The switching device especially preferably controls the optional operation of the first light source or the second light source over the at least one (joint) electrical line. The switching device is especially preferably designed as an electrical switching device, for example, as an H bridge.

If the instrument part is designed as a medical or dental handpiece, as is described above, then the lighting device is preferably disposed on or adjacent to a head part of the handpiece, in which the tool holder for the releasably connectable tool is mounted. In particular the lighting device comprises a plurality of optical semiconductor elements positioned in a ring around a tool receptacle opening of the head part.

Alternatively, the instrument part with the memory device, in particular with the microcontroller, does not comprise a lighting device but instead comprises only at least one (joint) electrical line, which is provided not only for supplying electrical power to the memory device, but which is also provided for supplying electrical power to a lighting device. The lighting device is disposed in another element, which is or can be connected to the instrument part with the memory device, so that the lighting device can be supplied with electrical power over the at least one (joint) electrical line.

According to an embodiment, no more than two (joint) electrical lines are provided for supplying electrical power to the lighting device for operating the lighting device and for supplying electrical power to the memory device for operating the memory device and for transmitting identification data and/or operating data and/or care data between the memory device and the control, regulating or supply unit connectable to the instrument part. Both the supply of electrical power to the lighting device and to the memory device and the data transmission thus take place exclusively by way of these two (joint) electrical lines. This embodiment is thus the simplest or optimal embodiment with respect to the design of the medical or dental instrument part, the number of electrical contacts on the coupling device and the space required.

According to an alternative embodiment, at least one separate line is provided for transmitting identification data and/or operating data and/or care data between the memory device and the control, regulating or supply unit that can be connected to the instrument part. This separate line (hereinafter also referred to as a data line) is thus, preferably exclusively provided for data transmission between the memory device and the control, regulating or supply unit, but it is not provided for the supply of electrical power to the lighting device and the memory device. The separate data line may be designed, for example, as an electrical line for transmitting electrical (data) signals or as an optical line, for example, as a glass fiber for transmitting optical (data) signals. The data line especially preferably forms a direct connection between the microcontroller of the memory device of the instrument part and the control, regulating or supply unit, in particular another microcontroller disposed in the control, regulating or supply unit.

This alternative embodiment thus preferably comprises three lines for supplying electrical power to the lighting device and to the memory device and for transmitting the identification data and/or operating data and/or care data between the memory device and the control, regulating or supply unit. These three lines in particular include at least two electrical lines for supplying electrical power to the lighting device and to the memory device and optionally a third electrical or optical line for data transmission. Accordingly, three electrical contacts or two electrical contacts and one optical contact are provided on the coupling device of the instrument part, wherein each contact is connected a corresponding one of the three lines.

The lighting device and the memory device are preferably disposed in parallel electrically with the microcontroller, in particular including a voltage device assigned to the memory device.

Preferably, an electrical switching element is provided which is assigned to the memory device in particular and which is designed to trigger changes in an electrical current parameter, in particular the electrical voltage for transmission of identification data and/or operating data and/or care data between the memory device and the control, regulating or supply unit that can be connected to the instrument part. The electrical switching element is preferably provided for supporting the readout or for reading out data from the memory device, in particular for transmitting data from the memory device to the control, regulating or supply unit. The electrical switching element preferably opens and closes a circuit between the memory device and the control, regulating or supply unit so that an electrical current parameter, in particular the electrical voltage is variable, for example, an electrical current parameter of the electrical power for supplying power to the lighting device and the memory device. The electrical switching element is preferably connected electrically to the at least one (joint) electrical line. The at least one (joint) electrical line is preferably part of this circuit. As will be described in detail below, the control, regulating or supply unit is preferably designed to receive the change in the electrical current parameter, wherein the change in the electrical parameter and/or the reaction of the control, regulating or supply unit define(s) the transmitted identification data and/or operating data and/or care data, in particular digitally.

The electrical switching element is preferably designed to short circuit the shunt resistor described in the following paragraph for readout of data from the memory device.

A shunt resistor, in particular one assigned to the memory device, is preferably provided and is designed to process changes in the electrical amperage for transmission of identification data and/or operating data and/or care data between the memory device and the control, regulating or supply unit that can be connected to the instrument part. The shunt resistor is preferably provided for or supports the storage of data in the memory device, in particular for transmitting data from the control, regulating or supply unit to the memory device. The shunt resistor preferably converts values of the electrical amperage of the control, regulating or supply unit which (digitally) define identification data and/or operating data and/or care data, into voltage values which can be processed by the memory device and which (digitally) define identification data and/or operating data and/or care data. The shunt resistor is preferably electrically connected to the at least one (joint) electrical line.

Alternatively or additionally, the shunt resistor is preferably designed for monitoring the current for the lighting device, in particular for the at least one optical semiconductor element. In particular the shunt resistor prevents the lighting device from being supplied with an electrical amperage that is too high.

Preferably, a device for voltage processing is provided which is designed to supply a constant electrical voltage to the memory device, in particular the microcontroller and which is assigned to the memory device, in particular the microcontroller. In particular the voltage processing device forms a constant voltage source for the memory device, in particular the microcontroller. The voltage processing is preferably electrically connected to a power source, in particular to an electrical constant current source in the control, regulating or supply unit, in particular being connected via at least one (joint) electrical line. The energy source, in particular the constant current source in the control, regulating or supply unit, preferably supplies electrical power to the voltage processing device. The voltage processing device is preferably designed so that the memory device, in particular the microcontroller is supplied with a lower electrical voltage than the lighting device. The voltage processing device is preferably connected in series to the memory device.

Preferably, a device for monitoring the voltage is provided which is assigned to the lighting device and which is designed to monitor the electrical voltage supplied to the lighting device. The voltage monitoring comprises in particular a voltage divider, which monitors the input voltage on the instrument part. The voltage divider has, for example, two electrical resistors, which are connected to the microcontroller of the memory device.

According to an embodiment, the instrument part comprises at least one sensor, which is designed to detect the operating state of the instrument part and to generate a sensor signal, preferably an electrical signal, wherein the at least one sensor is electrically connected to the at least one (joint) electrical line so that the sensor signal of the sensor and/or the electrical power for operating the sensor is/are transmissible over the at least (joint) electrical line.

The sensor comprises, for example, a temperature sensor for measuring the temperature of the instrument part or of a portion thereof or of at least a component disposed in the instrument part, in particular a component that can be set in motion by a drive element, for example, a bearing. The temperature sensor comprises in particular an electrically operable temperature sensor, for example, a temperature sensor having a material whose electrical resistance changes with the temperature (e.g., NCT temperature sensor) or an infrared temperature sensor.

Alternatively, the sensor comprises a speed sensor, for example, for measuring the rotational speed of a drive element of the instrument part or a tool that can be connected thereto. The speed sensor is designed, for example, as an inductive, capacitive or optical speed sensor.

The sensor may of course also be designed to measure other parameters and may comprise, for example, a sensor for measuring power, force or pressure, torque, light intensity or wavelength, etc.

The sensor signal is preferably sent over the at least one (joint) electrical line, or alternatively, over the separate data line described above to the control, regulating or supply unit, in particular to a microcontroller disposed therein. The at least one sensor is thus connected in particular via the at least one (joint) electrical line or via the separate data line to the control, regulating or supply unit in such a way that the control, regulating or supply unit receives a sensor signal and processes it. In particular the control, regulating or supply unit is designed to control or regulate the instrument part based on a sensor signal received from the at least one sensor or to supply said instrument part, for example, with an operating medium.

According to an embodiment, a medical or dental treatment device is provided, comprising: a medical or dental instrument part as described above or below, an electrical power source, in particular a constant current source, which is designed to supply the lighting device and the memory device of the instrument part with electrical power, and a control, regulating or supply unit, which is designed for exchanging identification data and/or operating data and/or care data of the instrument part with the memory device of the instrument part. The instrument part and the control, regulating or supply unit are preferably releasably connected to one another by the coupling device.

Another microcontroller, which is connected to the microcontroller of the instrument part is preferably provided in the control, regulating or supply unit, wherein the at least one (joint) electrical line forms a part of this connection. Preferably the power source is also disposed in the control, regulating or supply unit and in particular is connected electrically to the lighting device and the memory device by the at least one (joint) electrical line.

As already described above, the power source, in particular the constant current source, supplies the lighting device with a constant amperage. The memory device, in particular the microcontroller, which requires a constant electrical voltage is supplied with electrical power from the power source which is designed preferably as a constant current source via a device for voltage processing assigned to the memory device. The device for voltage processing is designed to supply a constant electrical voltage to the memory device.

Preferably the control, regulating or supply unit, in particular its microcontroller is designed to detect or recognize changes in the electrical load or the electrical voltage, which are in particular triggered by the switching element, for readout of the identification data and/or operating data and/or care data stored in the memory device.

As already described above, the electrical switching element preferably opens and closes a circuit between the memory device and the control, regulating or supply unit and in particular short-circuits the shunt resistor assigned to the memory device, so that an electrical current parameter, in particular the electrical voltage, which defines the identification data and/or operating data and/or care data (digitally) can be varied. The control, regulating or supply unit, in particular its microcontroller is/are designed to detect or recognize the changes or fluctuations triggered by the switching element. The change in the current parameter and/or the equalization of these fluctuations in the electrical current parameter are detected by the microcontroller of the control, regulating or supply unit and the identification data and/or operating data and/or care data transmitted from the memory device is thereby derived.

The electrical power source, in particular the constant current source and/or the control, regulating or supply unit is/are preferably designed to vary the electrical amperage, which can be supplied to the shunt resistor, which in particular is assigned to the memory device, and to the memory device for transmission of data to the memory device. The microcontroller of the control, regulating or supply unit is designed in particular to trigger or control the change in the electrical amperage. The change in amperage defines, digitally in particular, the identification data and/or operating data and/or care data. As described above, a shunt resistor preferably converts the values of the electrical amperage of the control, regulating or supply unit, which define identification data and/or operating data and/or care data, into electrical voltage values, which can be received and processed by the microcontroller of the instrument part so that the microcontroller can store data on the memory element of the memory device.

The control, regulating or supply unit is preferably designed to operate the instrument part based on identification data and/or operating data and/or care data stored in the memory device and read out of the memory device and/or on the basis of the sensor signal received from the at least one sensor. For example, the control, regulating or supply unit is designed to supply the drive power coordinated with this instrument part on the basis of this data and/or to supply at least a certain medium and/or a certain amount of one or more media.

The control, regulating or supply unit is preferably designed to transmit data to the instrument part, for example, with respect to the duration of operation of the instrument part, the type of use thereof and/or the type and/or duration of the cleaning and/or care thereof.

According to an embodiment a method for operating a medical or dental instrument part or a medical or dental treatment device is provided, in which at least one (joint) electrical line supplies electrical power to a lighting device that is provided on the instrument part or is or can be connected to the instrument part for operation of the lighting device and also supplies electrical power to a memory device for operation of said memory device.

Preferably no more than two electrical lines supply electrical power to the lighting device for operation of the lighting device and to the memory device for operation of the memory device and transmit the identification data and/or operating data and/or care data between the memory device and the control, regulating or supply unit that can be connected to the instrument part. Alternatively, at least one separate line (data line) transmits the identification data and/or operating data and/or care data, in particular directly, between the memory device and the control, regulating or supply unit that can be connected to the instrument part. The data line is optionally designed as an electrical line, which transmits the data in the form of electrical signals or as an optical line, which transmits the data in the form of optical signals.

The at least one (joint) electrical line preferably additionally transmits a sensor signal of the sensor in the instrument part and/or electrical power for operating the sensor as described above.

The control, regulating or supply unit, in particular its microcontroller, preferably detect(s) or recognize(s) changes in an electrical current parameter, in particular the electrical voltage caused by the switching element for readout of the identification data and/or operating data and/or care data stored in the memory device. The microcontroller of the control, regulating or supply unit detects the change in the electrical current parameter and/or the equalization of these fluctuations and therefrom recognizes the identification data and/or operating data and/or care data transmitted by the memory device as described above.

For transmitting data to the memory device the electrical power source, in particular the constant current source and/or the control, regulating or supply unit preferably vary/varies the electrical amperage, which is supplied to the shunt resistor and to the memory device. The shunt resistor preferably converts the values of the electrical amperage of the control, regulating or supply unit, which define the identification data and/or operating data and/or care data, into electrical voltage values, which define identification data and/or operating data and/or care data (digitally). These electrical voltage values are received or processed and stored in the memory element by the microcontroller of the instrument part, as described above.

The control, regulating or supply unit preferably operates the instrument part on the basis of identification data and/or operating data and/or care data stored in the memory device and read out of the memory device and/or on the basis of the sensor signal received from the at least one senor, as described above.

These and other embodiments will be described below with reference to the following drawings.

BRIEF DESCRIPTION OF THE DRAWINGS

FIG. 4 shows a schematic diagram of a second embodiment of an electrical switching circuit or current circuit having at least one joint electrical line for supplying a lighting device and a memory device.

FIGS. 5A-5C show three different embodiments of a lighting device and a sensor for an electrical switching circuit or current circuit of FIG. 4 or 5.

DETAILED DESCRIPTION

Figure 1:
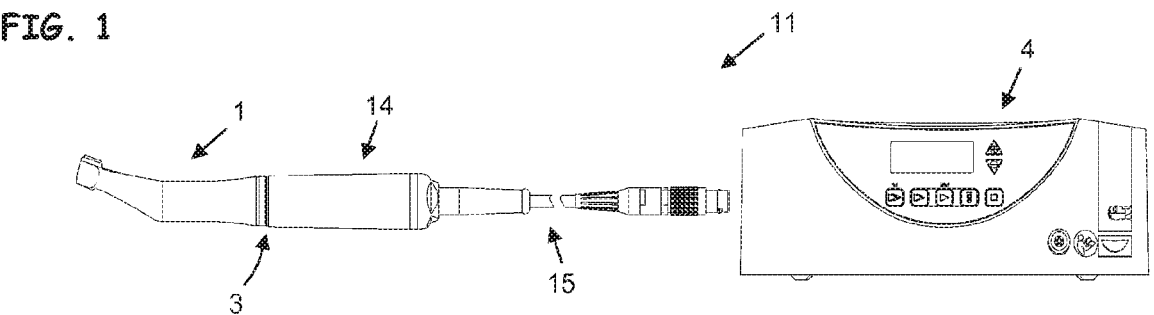
FIG. 1 shows a medical or dental treatment device comprising: a medical or dental instrument part with a lighting device, a memory device and at least one joint electrical line for supplying electrical power to the lighting device and the memory device, a drive device, a supply tube and a control, regulating or supply unit with an electrical power source for supplying electrical power to the lighting device and to the memory device.

FIG. 1 shows a medical or dental treatment device 11, comprising a medical or dental instrument part 1, a drive unit 14, a control, regulating or supply unit 4 and a supply tube 15 connecting the instrument part 1 to the control, regulating or supply unit 4. The instrument part 1 is releasably connected to the control, regulating or supply unit 4 by a coupling device 3.

Figure 2:
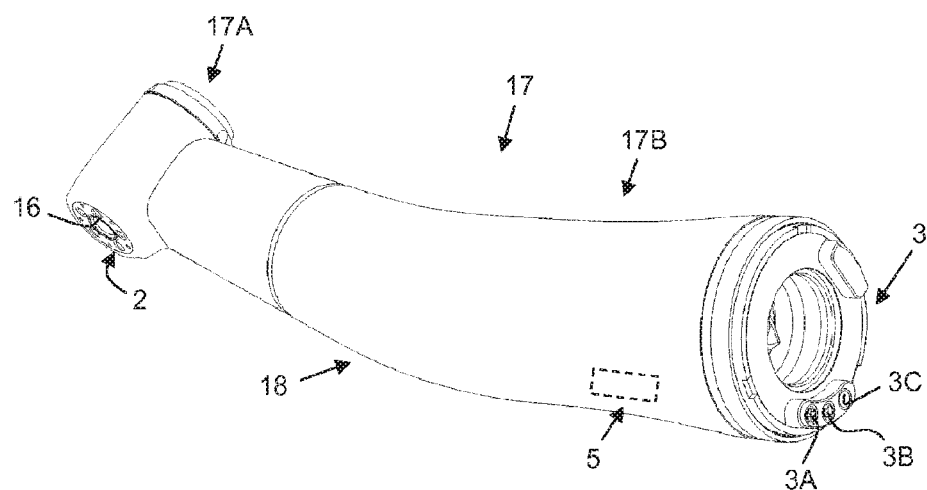
FIG. 2 shows the medical or dental instrument part of FIG. 1.

The instrument part 1 shown on an enlarged scale in FIG. 2 is formed by a bent handpiece or contra-angle handpiece 17. The handpiece 17 comprises a handpiece head 17A, in which a tool holder for fastening a tool, releasably in particular, is disposed as well as a handle part 17B for holding the handpiece 17 with one hand. The coupling device 3 and/or at least a portion thereof is/are disposed on the free or proximal end of the handle part 17B.

The drive unit 14 comprises, for example, an electric motor or an air motor, designed as separate components releasable from the handpiece 17 (as shown in FIG. 1) or integrated into the handpiece 17, However, the drive unit 14 may also comprise an impeller disposed in the handpiece 17, in particular in the handpiece head 17A and driven by a propellant gas. The handpiece 17 may thus be motor operated and may have at least one driveshaft for transmitting a drive movement to the tool or may be designed to be operated by propellant gas with an impeller. In both cases the handpiece 17 comprises at least one drive element that can be set in rotation for driving a tool that is connectable to the handpiece.

The handpiece 17 additionally comprises a lighting device 2, which is preferably disposed on the handpiece head 17A or adjacent thereto. The lighting device 2 shown in FIG. 2 comprises in particular a plurality of optical semiconductor elements (LEDs) disposed in a ring around the tool receptacle opening 16 of the handpiece head 17A.

In addition, openings for dispensing a medium, for example, water and/or air, are preferably disposed around the tool receptacle opening 16, preferably in alternation with the optical semiconductor elements. The openings for dispensing a medium are connected by at least one media line in the handpiece 17 to the control, regulating or supply unit 4 for supplying at least one medium.

In addition, a memory device for storing identification data and/or operating data and/or care data of the instrument part 1 or the handpiece 17 and which can be operated with electric power is disposed in the instrument part 1 or the handpiece 17. The memory device 5 may be disposed in the handpiece head 17A or in the handle part 17B or one part of the memory device 5 may be provided in the handpiece head 17A and another in the handle part 17B. Within the handle part 17B the memory device 5 or a portion thereof is disposed, for example, on its proximal or free end, in particular in or on the coupling device 3, in a section of the handle part 17B connected directly to the handpiece head 17A or in a bend 18 of the handle part 17B.

Figure 3:
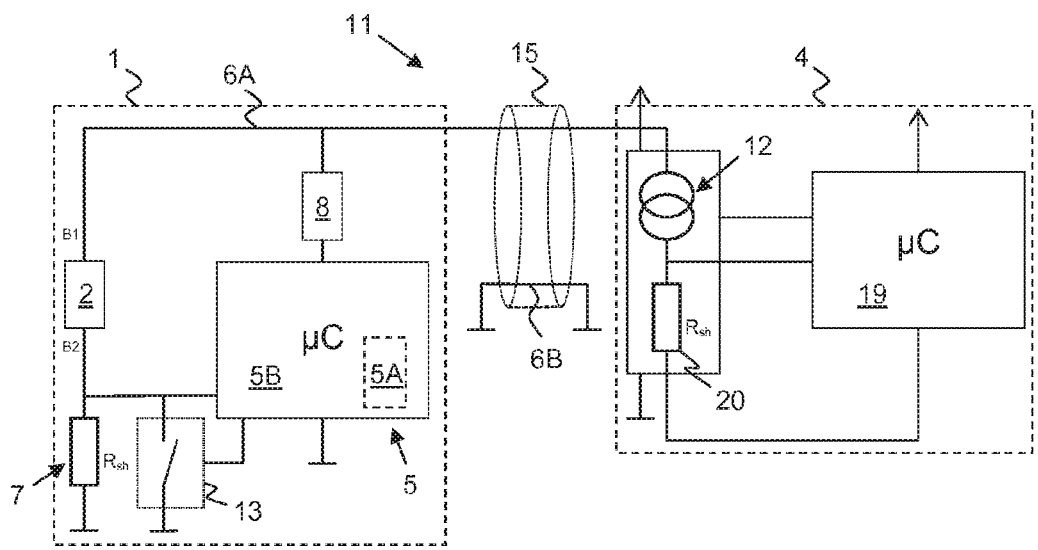
FIG. 3 shows a schematic diagram of a first embodiment of an electrical switching circuit or current circuit having at least one joint electrical line for supplying a lighting device and a memory device.

The memory device 5 comprises in particular a memory element 5A and a microcontroller 5B, in particular for operating the memory part 5A (see FIGS. 3 and 4).

As can be seen in particular from FIGS. 3 and 4, the instrument part 1 or the handpiece 17 additionally comprises at least one (joint) electrical line 6A, 6B, which is provided for supplying electrical power to the lighting device 2 provided on the handpiece 17 for operation of the lighting device 2 and for supply of electrical power to the memory device 5 for operation of the memory device 5. The at least one (joint) electrical line 6A, 6B connects the lighting device 2 and the memory device 5 to an electrical power source 12, in particular a constant current source, which is disposed in the control, regulating or supply unit 4 and which is designed to supply electrical power to the lighting device 2 and to the memory device 5. As can also be seen from FIGS. 3 and 4, the at least one (joint) electrical line 6A, 6B extends through the supply tube 15 up to or into the control, regulating or supply unit 4.

The at least one (joint) electrical line 6A, 6B thus electrically connects the lighting device 2 and the memory device 5 to the control, regulating or supply unit 4, in particular its electrical power source 12 and microcontroller 19, thereby forming an electrical switching circuit, control circuit, regulating circuit or supply circuit. Preferably the switching circuit, control circuit, regulating circuit or supply circuit also includes at least one sensor 10, as described in detail further below.

The electrical power source 12 in the form of a constant current source supplies electrical power at a constant electrical amperage to the instrument part 1 or the handpiece 17. For the lighting device 2 comprising at least one optical semiconductor, this forms an optimal power supply. However, the memory device 5, in particular the microcontroller 5B, requires an electrical supply at a constant electrical voltage. Therefore, a device 8 for voltage processing is provided, which is assigned to the memory device 5, in particular the microcontroller 59, and is designed to convert the electrical power at a constant electrical amperage received from the electrical power source 12 (over the electrical line 6A, 6B) into electrical power at a constant electrical voltage and to supply this converted power to the memory device 5. The device 8 for voltage processing is disposed in the instrument part 1 or the handle 17 in particular.

According to FIG. 3, two (joint) electrical lines 6A, 6B are provided for supplying electrical power to the lighting device 2 and to the memory device 5, as described above. In addition, the two electrical lines 6A, 6B are provided for transmitting identification data and/or operating data and/or care data between the memory device 5 and the control, regulating or supply unit 4 that can be connected to the instrument part 1 or handpiece 17. In other words, no more than the two (joint) electrical lines 6A, 6B are provided for supplying electrical power to the lighting device 2 and to the memory device 5 and for the data transmission. Accordingly, the control, regulating or supply unit 4 is designed for exchanging identification data and/or operating data and/or care data of the instrument part 1 with the memory device 5.

An electrical switching element 13, which is assigned to the memory device 5 is provided for transmission of identification data and/or operating data and/or care data from the memory device 5 to the control, regulating or supply unit 4, i.e., for readout of data from the memory device 5. As already described above, the switching element 13 is designed to cause or trigger changes of an electrical current parameter, in particular the electrical voltage or the electrical load, in particular by short circuiting a shunt resistor 7. The changes in the electrical current parameter (digitally) define the transmitted data. The control, regulating or supply unit 4, in particular its microcontroller 19 is/are designed to detect or equalize the changes in the electrical current parameter and, on this basis, to detect or read out the (digitally) transmitted identification data and/or operating data and/or care data.

In addition, a shunt resistor 7 is provided in the instrument part 1 or handpiece 17 which is designed to process changes in the electrical amperage for transmission of identification data and/or operating data and/or care data between the memory device 5 and the control, regulating or supply unit 4 that can be connected to the instrument part 1. As already described above, the shunt resistor 7 is provided for storing data in the memory device 5, in particular for transmitting data from the control, regulating or supply unit 4 to the memory device 5.

Another shunt resistor 20 is assigned to the control, regulating or supply unit 4, in particular to the microcontroller 19 of the control, regulating or supply unit 4.

According to FIG. 4 two (joint) electrical lines 6A, 6B are provided for supplying electrical power to the lighting device 2 and to the memory device 5, as described above. A separate line 6C or a data line is provided for transmission of identification data and/or operating data and/or care data between the memory device 5 and the control, regulating or supply unit 4 that can be connected to the instrument part 1 or handpiece 17. In other words, three lines are provided for supplying electrical power to the lighting device 2 and to the memory device 5 and for the data transmission, namely the two (joint) electrical lines 6A, 6B for supplying electrical power and the separate line 6C for transmitting the data as described above.

The separate data line 6C may be embodied as an electrical line for transmitting electrical (data) signals or as an optical line, for example, as a glass fiber for transmitting optical (data) signals. The separate line 6C extends through the instrument part 1 or the handpiece 17 and the supply tube 15 up to or into the control, regulating or supply unit 4.

Electrical contacts 3A, 3B, which are connected to the at least one joint electrical line 6A. 6B, are provided on the coupling device 3 of the instrument part 1 or of the handpiece 17, in particular on the end face of the coupling device 3 (see FIG. 2). These releasable electrical contacts 3A, 39 connect the lighting device 2 and the memory device 5 electrically to the control, regulating or supply unit 4, in particular to the power source 12 and microcontroller 19 thereof. If only two joint electrical lines 6A, 69 are provide for transmitting the electrical power and the data, as described above, then accordingly only these two electrical contacts 3A, 3B are provided on the coupling device 3. If at least one separate optical or electrical line 6C is provided for transmitting identification data and/or operating data and/or care data, then another optical or electrical contact 3C, which is connected to this at least one separate line 6C for the data transmission, is provided accordingly.

The at least one electrical contact or contacts are preferably releasably connected to the control, regulating or supply unit 4. The at least one electrical contact is, for example, designed as a pin-shaped electrical contact, as a spring contact, as a sliding contact or as an annular electrical contact surrounding a component of the coupling device.

Preferably at least one sensor 10 is provided in the medical or dental instrument part 1 or handpiece 17 which is designed to detect an operating state of the instrument part 1 or the handpiece 17 and to generate a sensor signal. The sensor 10 comprises, for example, a temperature sensor or a speed sensor for measuring the rotational speed of a drive element of the instrument part 1/handpiece 17, FIGS. 5A-5C show different arrangements of the sensor 10.

The at least one sensor 10 is electrically connect to the at least one electrical line 6A, 6B so that the sensor signal of the sensor 10 and/or electrical power for operating the sensor 10 can be transmitted over the at least one electrical line 6A, 6B.

The at least one sensor 10 is preferably also electrically connected to the memory device 5, in particular to the microcontroller 5B, so that a sensor signal of the sensor 10 in particular can be forwarded to the memory device 5. The memory device 5, in particular the microcontroller 5B is/are optionally designed (1) to forward the (analog) sensor signal of the sensor 10 preferably to the control, regulating or supply unit 4, in particular to its microcontroller 19, or (2) to convert the analog sensor signal into a digital signal and to send it to the control, regulating or supply unit 4, in particular to its microcontroller 19, or (3) to receive and process the (analog) sensor signal of the sensor 10 and to operate, regulate or control the instrument part 1/handpiece 17 or a component thereof, based on the sensor signal. Preferably, the sensor signal is forwarded to the control, regulating or supply unit 4 according to (1) or (2) over at least one of the lines 6A, 6B and 6C.

In the embodiment of FIG. 5A, the sensor 10, preferably a sensor for measuring the rotational speed, is disposed electrically in series with the lighting device 2. In the embodiment of FIG. 5B, the sensor 10, preferably a sensor for measuring the temperature, is disposed in parallel electrically with the lighting device 2. In both embodiments, the sensor 10 and the lighting device 2 have a joint electrical power source 12 and they are electrically connected to the electrical lines 6A, 6B.

In the embodiment of FIG. 5C, the sensor 10, preferably a sensor for measuring the temperature, and the lighting device 2 are connected to different electrical power sources for supplying them with electrical power.

The invention is not limited to the embodiments illustrated and described here. Furthermore, all the features of all the embodiments that are described and shown here can be combined with one another.

What is claimed is:

1. A medical or dental instrument part, comprising:
   a coupling device for connecting the instrument part to a control, regulating or supply unit,
   a memory device that can be operated with electrical power for storing identification data and/or operating and/or care data of the instrument part, exactly two shared electrical lines which connect the memory device and a lighting device that is provided on the instrument part or is connectible to the instrument part to a shared electrical power source for supplying a shared electrical power to the lighting device and the memory device, wherein the exactly two shared electrical lines are configured (i) for supplying electrical power to the lighting device for operating the lighting device and (ii) for supplying electrical power to the memory device for operating the memory device and (iii) for transmitting identification data and/or operating data and/or care data between the memory device and the control, regulating or supply unit, a device for voltage processing which is assigned to the memory device and is configured to convert the voltage of the shared electrical power received from the shared electrical power source for use by the memory device, a shunt resistor which is assigned electrically in parallel to the memory device and is configured to process changes in an electrical current parameter for transmission of identification data and/or operating data and/or care data between the memory device and the control, regulating or supply unit that can be connected to the instrument part, and an electrical switching element which is assigned to the memory device and is configured to trigger changes in the electrical current parameter by selectively bypassing the shunt resistor.

2. The medical or dental instrument part according to claim 1, wherein the memory device comprises a memory element and a microcontroller.

3. The medical or dental instrument part according to claim 1, wherein the device for voltage processing is configured to receive the shared electrical power from the shared electrical power source having a constant electrical amperage, to convert the shared electrical power having the constant amperage into electrical power at a constant electrical voltage, and to supply the converted electrical power to the memory device.

4. The medical or dental instrument part according to claim 1, comprising a device for monitoring voltage which is assigned to the lighting device and is configured to monitor the electrical voltage supplied to the lighting device.

5. The medical or dental instrument part according to claim 1, comprising at least one sensor which is configured to detect an operating state of the instrument part and to generate a sensor signal, wherein the at least one sensor is electrically connected to the exactly two shared electrical lines so that the sensor signal of the sensor and/or electrical power for operating the sensor can be transmitted over the exactly two shared electrical lines.

6. A medical or dental treatment device, comprising a medical or dental instrument part having:

a coupling device for connecting the instrument part to a control, regulating or supply unit, a memory device that can be operated with electrical power for storing identification data and/or operating and/or care data of the instrument part, and exactly two shared electrical lines which connect to the memory device and to a lighting device that is provided on the instrument part or can be connected to the instrument part for operating the lighting device, wherein the exactly two shared electrical lines are configured for (i) supplying electrical power to the lighting device for operating the lighting device and (ii) for supplying electrical power to the memory device for operating the memory device and (iii) for transmitting identification data and/or operating data and/or care data between the memory device and the control, regulating or supply unit, a shared electrical power source for supplying electrical power at a constant electrical amperage to the lighting device and to the memory device via the exactly two shared electrical lines, a shunt resistor which is assigned electrically in parallel to the memory device and is configured to process changes in an electrical current parameter for transmission of the identification data and/or the operating data and/or the care data between the memory device and the control, regulating or supply unit that can be connected to the instrument part, and an electrical switching element which is assigned to the memory device and is configured to trigger changes in the electrical current parameter by selectively bypassing the shunt resistor for transmitting the identification data and/or the operating data and/or the care data between the memory device and the control, regulating or supply unit, wherein the memory device exchanges identification data and/or operating data and/or care data of the instrument part via the exactly two shared electrical lines with the control, regulating or supply unit.

7. The medical or dental treatment device according to claim 6, wherein the shared electrical power source comprises a shared constant current source for supplying shared electrical power at a constant electrical amperage, further comprising a device for voltage processing of the medical or dental instrument assigned to the memory device and configured to convert the shared electrical power having the constant electrical amperage into electrical power at a constant electrical voltage and to supply the converted power to the memory device.

8. The medical or dental treatment device according to claim 6, wherein the control, regulating or supply unit is configured to operate the instrument part on the basis of identification data and/or operating data and/or care data stored in the memory device and read out of the memory device, and/or on the basis of a sensor signal received from at least one sensor of the medical or dental instrument part which is electrically connected to the exactly two shared electrical lines.

9. A medical or dental handpiece, comprising:

a coupling device which couples the medical or dental handpiece to a supply tube for connection of the medical or dental handpiece to a control, regulating or supply unit, a memory device comprising a memory element and a microcontroller, arranged on the medical or dental handpiece and operable with electrical power for storing identification data and/or operating and/or care data of the medical or dental handpiece, exactly three electrical lines, wherein a first shared electric line and a second shared electric line of the exactly three electric lines connect to the memory device and to a lighting device that is provided on the medical or dental handpiece or can be connected to the medical or dental handpiece and supply electrical power from a shared electrical power source which provides electrical power having a constant electrical amperage to the lighting device for operating the lighting device and to the memory device for operating the memory device, and wherein a third electric line of the exactly three electric lines connects to the memory device for transmitting identification data and/or operating data and/or care data between the memory device and the control, regulating or supply unit, a device for voltage processing which is assigned to the memory device and is configured to convert the voltage of the electrical power received from the shared electrical power source for the memory device, wherein the device for voltage processing converts the electrical power having a constant electrical amperage into electrical power at a constant electrical voltage and supplies the converted power to the memory device, and at least one sensor which is arranged on the handpiece and configured to detect a rotational speed and to generate a sensor signal, wherein the at least one sensor is electrically connected in series with the lighting device.

10. The medical or dental handpiece according to claim 9, wherein the first shared electric line connects to a first electrical contact on an end face of the coupling device of the medical or dental handpiece, the second shared electric line connects to a second electrical contact on the end face of the coupling device of the medical or dental handpiece and the third electric line connects to a third electrical contact on the end face of the coupling device of the medical or dental handpiece, wherein the first, second and third electrical contacts can be coupled to the supply tube for supply of electrical power to the lighting device and to the memory device and for transmission of identification data and/or operating data and/or care data between the memory device and the control, regulating or supply unit, wherein the first, second and third electrical contacts are arranged on a shared protrusion projecting from a ring-shaped end face of the coupling device which couples the medical or dental handpiece to a supply tube.

11. The medical or dental handpiece according to claim 9, wherein the shared electrical power source provides electrical power having a constant electrical amperage and the device for voltage processing converts the electrical power having a constant electrical amperage into electrical power at a constant electrical voltage and supplies the converted electrical power to the memory device.

12. The medical or dental treatment device according to claim 11, wherein the shared electrical power source comprises a shared constant current source for supplying shared electrical power at a constant electrical amperage, further comprising a device for voltage processing of the medical or dental instrument part assigned to the memory device and configured to convert the shared electrical power having the constant electrical amperage into electrical power at a constant electrical voltage and to supply the converted power to the memory device.

13. A method for operating a medical or dental instrument part, comprising:

providing a coupling device for connecting the instrument part to a control, regulating or supply unit;

providing a memory device that can be operated with electrical power for storing identification data and/or operating data and/or care data of the instrument part;

providing exactly two shared electrical lines (i) to supply electrical power to a lighting device that is provided on the instrument part or can be connected to the instrument part for operation of the lighting device and (ii) to supply electrical power to the memory device for operation of the memory device and (iii) to transmit identification data and/or operating data and/or care data between the memory device and the control, regulating or supply unit providing a shared electrical power source comprising a shared constant current source for supplying electrical power at a constant electrical amperage to the memory device and to the lighting device via the exactly two shared electrical lines, and providing a device for voltage processing which is assigned to the memory device and configured to convert the electrical power provided by the shared constant current source and having a constant electrical amperage into electrical power at a constant electrical voltage and to supply the converted power to the memory device, providing a shunt resistor which is assigned electrically in parallel to the memory device and is configured to process changes in an electrical current parameter for transmission of the identification data and/or the operating data and/or the care data between the memory device and the control, regulating or supply unit that can be connected to the instrument part, and providing an electrical switching element which is assigned to the memory device and is configured to trigger changes in the electrical current parameter by selectively bypassing the shunt resistor for transmitting the identification data and/or the operating data and/or the care data between the memory device and the control, regulating or supply unit.

14. A medical or dental handpiece, comprising:

a coupling device which couples the medical or dental handpiece to a supply tube for connection of the medical or dental handpiece to a control, regulating or supply unit, a memory device comprising a memory element and a microcontroller, arranged on the medical or dental handpiece and operable with electrical power for storing identification data and/or operating and/or care data of the medical or dental handpiece, exactly three electrical lines, wherein a first shared electric line and a second shared electric line of the exactly three electric lines connect to the memory device and to a lighting device that is provided on the medical or dental handpiece or can be connected to the medical or dental handpiece and supply electrical power from a shared electrical power source which provides electrical power having a constant electrical amperage to the lighting device for operating the lighting device and to the memory device for operating the memory device, and wherein a third electric line of the exactly three electric lines connects to the memory device for transmitting identification data and/or operating data and/or care data between the memory device and the control, regulating or supply unit, a device for voltage processing which is assigned to the memory device and is configured to convert the voltage of the electrical power received from the shared electrical power source for the memory device, wherein the device for voltage processing converts the electrical power having a constant electrical amperage into electrical power at a constant electrical voltage and supplies the converted power to the memory device, and at least one sensor which is arranged on the handpiece and configured to detect a temperature and to generate a sensor signal, wherein the at least one sensor is electrically connected in parallel with the lighting device.

15. The medical or dental handpiece according to claim 14, wherein the shared electrical power source provides electrical power having a constant electrical amperage and the device for voltage processing converts the electrical power having a constant electrical amperage into electrical power at a constant electrical voltage and supplies the converted electrical power to the memory device.

16. The medical or dental handpiece according to claim 14, comprising a device for monitoring voltage which is assigned to the lighting device and is configured to monitor the electrical voltage supplied to the lighting device.

17. The medical or dental handpiece according to claim 14, wherein the first shared electric line and the second shared electric line of the exactly three electric lines connect the at least one sensor to the shared electrical power source to provide electrical power to the at least one sensor.

18. The medical or dental handpiece according to claim 9, wherein the first shared electric line and the second shared electric line of the exactly three electric lines supply power to the lighting device and in turn to the at least one sensor connected in series to the lighting device.

\* \* \* \* \*